US006413988B1

(12) United States Patent
De Proost

(10) Patent No.: US 6,413,988 B1
(45) Date of Patent: Jul. 2, 2002

(54) PRUCALOPRIDE ORAL SOLUTION

(75) Inventor: Eddy André Josée De Proost, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/980,848

(22) PCT Filed: Apr. 20, 2000

(86) PCT No.: PCT/EP00/03739

§ 371 (c)(1),
(2), (4) Date: Oct. 26, 2001

(87) PCT Pub. No.: WO00/66170

PCT Pub. Date: Nov. 9, 2000

(30) Foreign Application Priority Data

Apr. 29, 1999 (EP) ............................................. 99201335

(51) Int. Cl.$^7$ .............................................. A61K 31/445
(52) U.S. Cl. ...................................................... 514/320
(58) Field of Search .......................................... 514/320

(56) References Cited

FOREIGN PATENT DOCUMENTS

| EP | 0 389 037 A1 | 9/1990 |
| EP | 0 445 862 A2 | 9/1991 |
| WO | WO 96/16060 A1 | 5/1996 |
| WO | WO 00/30640 a1 | 6/2000 |

*Primary Examiner*—Raymond Henley, III
(74) *Attorney, Agent, or Firm*—Ellen Ciambrone Coletti

(57) ABSTRACT

The present invention is concerned with the an oral aqueous solution comprising prucalopride or pharmaceutically acceptable acid addition salts thereof having good organoleptic properties.

9 Claims, No Drawings

PRUCALOPRIDE ORAL SOLUTION

CROSS REFERENCE TO RELATED APPLICATIONS

This application is the national stage, 371, of Application No. PCT/EP00/03739 filed Apr. 20, 2000, which application claims priority from EP application No. 99201335.9, filed Apr. 29, 1999.

The present invention concerns an oral aqueous solution comprising prucalopride or pharmaceutically acceptable acid addition salts thereof having good organoleptic properties.

Prucalopride, which is the generic name for the (1:1) succinic acid addition salt of 4-amino-5-chloro-2,3-dihydro-N-[1-(3-methoxypropyl)-4-piperidinyl]-7-benzofuran-carboxamide, has enterokinetic properties, i.e. it has strong gastrointestinal prokinetic activity.

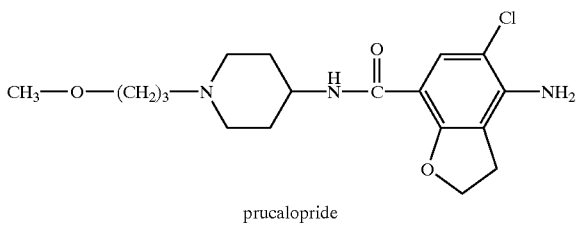

prucalopride

Prucalopride facilitates both cholinergic and non-cholinergic non-adrenergic (NANC) excitatory neurotransmission and stimulates colonic motility and defecation in animals. It has no affinity for $5\text{-HT}_{2A}$ and $5\text{-HT}_3$ receptors but is a potent and selective agonist of $5\text{-HT}_4$ receptors. Prucalopride induces giant contractions in the colon that are propagated over the length of the colon as a peristaltic wave and therefore has significant motility enhancing effects on the large intestine.

Formulations comprising prucalopride are believed of potential use in the treatment of conditions associated with a poorly functioning bladder such as, e.g. urinary incontinence or urinary retention.

Prucalopride is generically described in EP-0,445,862-A1, published on Sep. 11, 1991, and is specifically disclosed in WO-96/16060, published on May 30, 1996.

Administration of an oral dosage form is the preferred route of administration for many pharmaceuticals because it provides for easy, low-cost administration. However some patients such as children or elderly people can have problems when requested to swallow a solid formulation such as a tablet or a capsule. Hence the development of a liquid oral formulation is therefore desirable since it offers improved patient compliance. EP-0,445,862-A1 discloses an oral solution which comprises prucalopride only in a generic way.

When an aqueous oral solution comprising prucalopride was prepared in accordance with example 22, p. 36, of EP-0,445,862-A2 and administered to a test group of 24 human volunteers in a blind study, it was found that such an oral solution had undesirable organoleptic properties, in particular most volunteers experienced an anaesthetizing feeling on the tongue.

Unexpectedly, it has been found that the prucalopride oral solutions according to the present invention containing benzoic acid do not give an anaesthetizing feeling on the tongue, and thus have acceptable organoleptic properties. Furthermore, the general perception of sweetness and taste were improved.

The term prucalopride as used herein comprises the free base form and the pharmaceutically acceptable acid addition salts thereof. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which prucalopride as well as the salts thereof, are able to form. Such solvates are for example hydrates, alcoholates and the like.

Preferred pharmaceutically acceptable acid addition salts of 4-amino-5-chloro-2,3-dihydro-N-[1-(3-methoxypropyl)-4-piperidinyl]-7-benzofuran-carboxamide are the hydrochloric acid (1:1) addition salt and the succinic acid (1:1) addition salt.

The solutions according to the present invention have a pH from 2 to 5, preferably from 3.5 to 4.5, most preferably about 4. The pH of the compositions is maintained by a buffer system. Buffer systems comprise mixtures of appropriate amounts of an acid such as phosphoric, succinic, tartaric, lactic, or citric acid, and a base, in particular sodium hydroxide or disodium hydrogen phosphate. Ideally, the buffer has sufficient capacity to remain in the intended pH range upon dilution with a neutral, a slightly acidic or a slightly basic beverage.

Preservatives are included in preparations to kill or inhibit the growth of micro-organisms inadvertently introduced during manufacture or use and are therefore essential ingredients. The choice of a suitable preservative for a preparation depends on pH, compatibility with other ingredients, the route of administration, dose and frequency of administration of the preparation, partition coefficients with ingredients and containers or closures, degree and type of contamination, concentration required, and rate of antimicrobial effect.

In addition to its advantageous organoleptic properties, benzoic acid is also a preservative and is used to prevent microbial spoilage of the oral prucalopride solutions in a concentration from 0.5 mg/ml to 3 mg/ml, preferably from 1 mg/ml to 2 mg/ml, most preferably 1.5 mg/ml.

The pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

The intense sweetener is conveniently employed in low concentrations. For example, in the case of sodium saccharin, the concentration may range from 0.01% to 0.1% (w/v) based on the total volume of the final formulation, and preferably is about 0.05% (w/v).

The bulk sweetener, such as sorbitol, can effectively be used in larger quantities ranging from about 10% to about 35% (w/v), preferably from about 15% to 30% (w/v), more preferably about 30 % (w/v).

When sorbitol is used as a bulk sweetener it is preferably used as an aqueous solution containing 70% (w/v) of sorbitol.

The pharmaceutically acceptable flavours which can mask the bitter tasting ingredients in the low-dosage formulations are preferably fruit flavours such as cherry, raspberry, black currant, strawberry flavour, caramel chocolate flavour, mint cool flavour, fantasy flavour and the like pharmaceutically acceptable strong flavours. Each flavour may be present in the final composition in a concentration ranging from 0.05% to 1% (w/v).

Combinations of said strong flavours are advantageously used. Preferably a flavour is used that does not undergo any change or loss of taste and colour under the acidic conditions of the formulation.

The subject solutions may be presented in art-known containers such as bottles, spray devices, sachets, and the like. Optionally, the solutions are manufactured in unit-dose containers, e.g. unit-dose sachets or unit-dose bottles. Further, the present invention relates to the preparation of the described solutions. The preparation involves the intimate mixing of the active ingredient with the carrier ingredients.

In general it is contemplated that a therapeutically effective amount of prucalopride would be from about 0.001 mg/kg to about 1 mg/kg body weight, preferably from about 0.01 mg/kg to about 0.5 mg/kg body weight. A method of treatment may also include administering prucalopride on a regimen of between two or four intakes per day.

The amount of prucalopride, or a pharmaceutically acceptable acid addition salt thereof, required as daily dose in treatment will vary not only with the route of administration, the nature of the condition being treated and the age, weight and condition of the patient and will ultimately be at the discretion of the attendant physician. In general, however, a suitable daily dose will be in the range of from about 0.05 to about 50 mg per day, in particular from about 0.1 to 20 mg per day, more particular from about 0.5 to 10 mg per day, preferably from 2 to 4 mg per day. A suitable daily dose for use in prophylaxis will generally be in the same range. It may be appropriate to administer the required dose as two, three, four or more sub-doses at appropriate intervals throughout the day. Administration can be before or after the intake of food (i.e. preprandial or postprandial).

EXPERIMENTAL SECTION

Example 1

Comparative Study

The perception of taste and aftertaste of 2 flavours (cherry flavour 2 and strawberry flavour) in combination with 2 sweeteners (sorbitol 70% (w/v) and sodium saccharin dihydrate) was rated. Therefore oral liquid formulations containing one of the two flavours were evaluated for sweetness, fruit taste, anaesthetizing feeling on the tonge and general perception by 24 volunteers in a blind study.

TABLE 1 composition of test formulations

| Compound | Formulation (1) Concentration | Formulation (2) Concentration |
| --- | --- | --- |
| cherry flavour 2 | X1 | — |
| strawberry flavour | — | Y2 |
| sorbitol (70% w/v) | X2 | Y2 |

TABLE 1-continued composition of test formulations

| Compound | Formulation (1) Concentration | Formulation (2) Concentration |
| --- | --- | --- |
| sodium saccharin dihydrate | X3 | Y3 |
| methyl parahydroxybenzoate | 1.8 mg | 1.8 mg |
| propyl parahydroxybenzoate | 0.2 mg | 0.2 mg |

In both formulations (1) and (2), sodium hydroxide was added to adjust to pH to 4, and purified water was added to a total volume of 1 ml.

Two three-factor, two level full-factorial screening designs were applied to evaluate the effects of sweetness, fruit taste, anaesthetizing feeling and perception.

TABLE 1a independent variables and experimental factors of first series of formulations

| Factor | Concentration | Concentration |
| --- | --- | --- |
| X1 | 1 mg/ml | 3 mg/ml |
| X2 | 150 mg/ml | 300 mg/ml |
| X3 | 0.5 mg/ml | 1 mg/ml |

X1: concentration of cherry flavour 2
X2: concentration of sorbitol 70% (w/v)
X3: concentration of sodium saccharin dihydrate TABLE 1b independent variables and experimental factors of second series of formulations

| Factor | Concentration | Concentration |
| --- | --- | --- |
| Y1 | 1 mg/ml | 3 mg/ml |
| Y2 | 150 mg/ml | 300 mg/ml |
| Y3 | 0.5 mg/ml | 1 mg/ml |

Y1: concentration of strawberry
Y2: concentration of sorbitol 70% (w/v)
Y3: concentration of sodium saccharin dihydrate Hence, two formulations (1) and two formulations (2) were submitted to the test panel of 24 volunteers.

The dependent (response) variables (sweetness, fruit taste, e feeling and general score) were scored on a scale of 1 to 10.

Overall, sodium saccharin dihydrate scored better in a concentration of 0.5 mg/ml, sorbitol 70% (w/v) in a concentration of 300 mg/ml.

Strawberry scored better than cherry flavour 2. Strawberry affected the sweetness less than cherry flavour 2 and the fruit taste was more pronounced.

However, an anaesthetizing feeling on the tongue was perceived with all formulations.

Because of the anaesthetizing feeling on the tongue, probably due to the use of parahydroxybenzoates (parabens) as preservative, another experiment was set up with benzoic acid as preservative.

Example 2

Comparative Study

Oral liquid formulations containing one of the two preservatives (parahydroxybenzoates or benzoic acid) were evaluated for sweetness, fruit taste and anaesthetizing feeling on the tongue and general perception by 6 volunteers in a blind study.

TABLE 2 composition of test formulations:

| Compound | Formulation (3) Concentration | Formulation (4) Concentration |
| --- | --- | --- |
| strawberry flavour | 3 mg | 3 mg |
| sorbitol (70% w/v) | Z1 | Z1 |
| sodium saccharin dihydrate | 0.5 mg | 0.5 mg |
| methyl parahydroxybenzoate | 1.8 mg | — |
| propyl parahydroxybenzoate | 0.2 mg | — |
| benzoic acid | — | 2 mg |

Z1: concentration of sorbitol 70% (w/v) is 150 mg/ml or 300 mg/ml

In both formulations (3) and (4), sodium hydroxide was added to adjust the pH to 4, and purified water was added to a total volume of 1 ml.

A user specified design was applied to evaluate the effects of sweetness, fruit taste and anaesthetizing feeling and general perception.

The dependent (respons) variables (sweetness, fruit taste, anaesthetizing feeling and general perception) were scored on a scale of 1 to 10. The data were analyzed using one-way ANOVA to determine significant differences between the individual means.

Overall, the anaesthetizing feeling was not observed in the presence of benzoic acid, whereas it was always observed in the oral solutions containing parabens (i.e. methyl parahydroxybenzoate and propyl parahydroxybenzoate).

Table 3 lists the composition most widely accepted and recommended by the panel of volunteers.

TABLE 3 preferred composition

| Compound | Formulation (3) Concentration | |
| --- | --- | --- |
| strawberry flavour | 3 mg | 0.3% (w/v) |
| sorbitol (70% w/v) | 300 mg | 30% (w/v) |
| sodium saccharin dihydrate | 0.5 mg | 0.05% (w/v) |
| benzoic acid | 2 mg | 0.2% (w/v) |

Sodium hydroxide was added to adjust the pH to 4, and purified water was added to a total volume of 1 ml.

Example 3

Oral Solution (0.2 mg/ml prucalopride)

The following solution comprises 0.2 mg/ml of prucalopride in its free base form as active ingredient, or 0.264 mg/ml of prucalopride as its succinic acid (1:1) addition salt.

| | |
| --- | --- |
| prucalopride succinic acid (1:1) addition salt | 264 mg |
| benzoic acid | 1500 mg |
| sorbitol (70% w/v) | 230 ml |
| sodium saccharin | 500 mg |
| strawberry flavour | 3000 mg |

+sodium hydroxide to adjust the pH to a value of 4

+purified water until a total volume of 1000 ml.

What is claimed is:

1. An oral aqueous solution having a pH ranging from 2 to 5 and comprising as active ingredient prucalopride, or a pharmaceutically acceptable acid addition salt thereof, and further containing benzoic acid.

2. An oral solution according to claim 1 wherein the amount of benzoic acid ranges from 0.5 mg/ml to 3 mg/ml.

3. An oral solution according to claim 1 wherein the pharmaceutically acceptable addition salt of prucalopride is the (1:1) succinic acid addition salt.

4. An oral solution according to claim 1 wherein the pharmaceutically acceptable addition salt of prucalopride is the (1:1) hydrochlorid acid addition salt.

5. An oral solution according to claim 1 wherein the pH ranges of from 3.5 to 4.5.

6. An oral solution according to claim 1 further comprising a bulk sweetener in a concentration range from 10% to 35% (w/v) and an intense sweetener in a concentration range from 0.01% to 0.05% (w/v).

7. An oral solution according to claim 6 wherein the bulk sweetener is sorbitol and the intense sweetener is sodium saccharin.

8. An oral solution according to claim 1 comprising the following ingredients:

| | |
| --- | --- |
| prucalopride succinic acid (1:1) addition salt | 264 mg |
| benzoic acid | 1500 mg |
| sorbitol (70% w/v) | 230 ml |
| sodium saccharin | 500 mg |
| strawberry flavour | 3000 mg |
| + sodium hydroxide to adjust the pH to a value of 4 | |
| +0 purified water until a total volume of 1000 ml. | |

9. A method of preparing an organoleptically acceptable and oral aqueous solution and comprising as active ingredient prucalopride or a pharmaceutically acceptable acid addition salt thereof, which comprises including benzoic acid in such solution, and adjusting the pH to range from about 2 to 5.

* * * * *